(12) United States Patent
Glasson et al.

(10) Patent No.: US 7,863,034 B2
(45) Date of Patent: Jan. 4, 2011

(54) MICROBIAL STREAKING DEVICE

(75) Inventors: John Glasson, Adelaide (AU); Lachlan Smith, Adelaide (AU)

(73) Assignee: Medvet Science Pty Ltd, Adelaide (AU)

( * ) Notice: Subject to any disclaimer, the term of this patent is extended or adjusted under 35 U.S.C. 154(b) by 1186 days.

(21) Appl. No.: 11/459,094

(22) Filed: Jul. 21, 2006

(65) Prior Publication Data

US 2007/0202564 A1    Aug. 30, 2007

(30) Foreign Application Priority Data

Jan. 22, 2004  (AU) .............................. 2004900276
Jan. 21, 2005  (WO) .............. PCT/AU2005/000079

(51) Int. Cl.
C12M 1/36    (2006.01)
C12M 1/38    (2006.01)
C12M 3/00    (2006.01)

(52) U.S. Cl. ................... 435/286.3; 435/30; 435/309.1; 422/102

(58) Field of Classification Search ............... 435/30, 435/286.3, 309.1; 422/102
See application file for complete search history.

(56) References Cited

U.S. PATENT DOCUMENTS

| | | | |
|---|---|---|---|
| 3,455,788 A | 7/1969 | Curry et al. | |
| 3,850,754 A | 11/1974 | Wilkins et al. | |
| 4,102,748 A | 7/1978 | Vacanti | |
| 4,287,301 A | 9/1981 | Astle | |
| 4,981,802 A | 1/1991 | Wylie et al. | |
| 6,291,234 B1 | 9/2001 | Raz et al. | |
| 6,521,190 B1 * | 2/2003 | Edens et al. | ................. 422/102 |
| 6,617,146 B1 | 9/2003 | Naccarato et al. | |
| 2004/0180427 A1 * | 9/2004 | Chang | ..................... 435/309.1 |

FOREIGN PATENT DOCUMENTS

| | | |
|---|---|---|
| CH | 555889 | 11/1974 |
| DE | 1617770 | 4/1971 |
| DE | 19826244 | 12/1999 |
| GB | 2255407 | 11/1992 |
| JP | S61-056899 | 4/1986 |
| JP | H02-027975 | 1/1990 |
| JP | H07-303472 | 11/1995 |
| JP | 08-166201 | 1/1998 |

(Continued)

OTHER PUBLICATIONS

International search report.

(Continued)

*Primary Examiner*—Walter D Griffin
*Assistant Examiner*—Shanta G Doe
(74) *Attorney, Agent, or Firm*—Buchanan Nipper (57) ABSTRACT

A streaker device for streaking a microbial inoculum for single colonies on the surface of a solid growth medium. The streaking device has a row of spaced apart contact surfaces for contact with the surface of the solid growth medium. The spaced apart contact surfaces are resiliently flexibly supported by a common support member so as to accommodate variations in depth of growth medium. The spaced apart contact surfaces may be provided on lowermost part of axially curved portions of plastics straps, that are angled backwardly. It is found that formation of a single band can give separation into single colonies. Also provided is an automatic streaking apparatus.

36 Claims, 7 Drawing Sheets

FOREIGN PATENT DOCUMENTS

| | | |
|---|---|---|
| JP | H10-004952 | 1/1998 |
| WO | WO0166686 | 3/2001 |
| WO | WO0190296 | 11/2001 |
| WO | WO02053698 | 7/2002 |

OTHER PUBLICATIONS

English Translation of WO0166686.
JPO Notification of Reason(s) for Refusal, Patent Application No. 2006-549784, mailed Sep. 7, 2010.

\* cited by examiner

MICROBIAL STREAKING DEVICE

This invention relates to a liquid sample streaker, and more particularly to a streaking brush for streaking samples on the surface of a solid growth medium for obtaining single microbial colonies, for example, from clinical specimens taken for medical diagnostic purposes, and to a method of streaking a liquid sample using the brush, and an apparatus for automated streaking of samples to obtain single colonies.

BACKGROUND OF THE INVENTION

The isolation of individual colonies of micro-organisms is a procedure that is important for many reasons in scientific endeavour, and is specifically important for identifying micro-organisms for medical diagnostic purposes. It is used for a number of different micro-organisms but principally bacteria.

Generally isolation of single colonies is performed manually by laboratory technicians who utilise a metal or plastics loop to make multiple streaks of an inoculum on a first band in a first direction of an agar plate and produce a second band of multiple streaks with a fresh or freshly sterilised loop crossing the first band, and typically also a third and fourth band. Typically, a non-oxidising metal (platinum or nichrome) loop is held within a holder and is sterilised by heating either in the flame of a bunsen burner or in an electric heater, the loop being rapidly cooled in air or on the edge of the agar based, solid medium being used before picking up the inoculum either from the first, second or third band or other source of the microorganism. Alternatively the technician may utilise disposable loops in a similar manner as described above.

One drawback is that the work is relatively tedious and requires employment of a skilled person to perform often hundreds of isolations at a time. This is costly and the highly repetitious nature of the work can lead to errors which may have severe consequences in a diagnostic setting.

There have been several suggestions for the automation of streaking for isolated colonies. Some of the suggestions such as in patent specifications GB 2025457, EP 073774, U.S. Pat. No. 3,962,040 and U.S. Pat. No. 3,623,958 use dilution spiralling or oscillation movement of a head connected by a tube to a container holding a suspension of microorganisms. These suggestions are not suitable for readily isolating colonies from large numbers of samples. Other suggestions are more technically advanced and disclose automated isolation systems for multiple samples with the capacity for streaking samples onto a range of different petri plates for differential testing, and include delivery mechanisms for retrieval of plates from storage and placing plates on a streaking station, examples of these are disclosed in patent specifications U.S. Pat. No. 4,981,802, U.S. Pat. No. 4,287,301, and U.S. Pat. No. 6,617,146.

None of these, however, particularly address the efficiency of the mechanism of spreading to produce single, isolated microbial colonies, all use a head with a narrow contact surface requiring multiple drawing motions, each representing a streak for each band. There have been suggestions for more efficient devices for streaking micro-organisms and in particular the provision of a distinctly separate surface that can sequentially be used to present a separate sterile portion to streak the first band, the second band and finally the third band. Two such disclosures namely patent specifications U.S. Pat. No. 4,010,077 and U.S. Pat. No. 4,687,746, whilst alleviating the need to sterilise the device between streaking separate bands, still require repetitive streaking for each band.

U.S. Pat. No. 4,102,748 discloses a spreader tool providing three relatively elongated surfaces for spreading three bands on a solid growth surface. Such a tool is however, not ideal for all types of inocula. Thus, where a liquid depot of the sample is provided, the use of this spreader tool will tend to carry with it a large quantity of the inoculum, as distinct to the multiple streaks formed by a loop where only a small sample of the liquid is carried, and thus the U.S. Pat. No. 4,102,748 tool in some samples may not give adequate dilution within the confines of a petri plate to obtain isolated colonies.

One of the problems associated with a wide head surface is that solid media is not always formed perfectly smooth or precisely level with the petri plate and therefore contact with a head in an automated system needs to have provision to accommodate such variation. The other major disadvantage of the device disclosed in U.S. Pat. No. 4,102,748 is that the device is designed for manual operation and there is no indication of how this device might be adapted to an high volume automated system.

SUMMARY OF THE INVENTION

In a first form of a first aspect the invention might be said to reside in a streaker device for streaking a microbial inoculum for single colonies on the surface of a solid growth medium, said streaking device having a row of spaced apart contact surfaces for contact with the surface of the solid growth medium and being resiliently flexibly supported by a common support member.

In a convenient form the contact surfaces are provided one each on a separate elongate member. Thus a plurality of elongate members may depend from the common support member. In an alternative form the spaced apart contact surfaces may be provided by spaced apart downwardly extending protrusion on a rigid transverse lowermost member which is resiliently flexibly linked to the common support member.

Each elongate member may be in the form of a fibre and the contact surface may be provided by a free end of the fibre. The fibres in each row may form a brush having a depth of more than one fibre. The free end of the fibre may present a curved surface to minimise the potential to cut into the surface of the growth medium, however, given the pliable nature of fibres it is anticipated that to some extent perhaps rounded sides of the fibres will ultimately contact the surface of the growth medium.

In a preferred form the elongate members are each a strap formed together with the remainder of the streaker device from plastics being moulded in one piece. Preferably the strap is flexible however it need not be, it can be relatively inflexible and apart from a flexible hinge region provided by a thinning in cross sectional dimension at the hinge region. The hinge region is preferably provided adjacent the common support member.

It is preferred that each elongate strap exhibits an axially curved portion at a lower part. The ends of the elongate straps are thus, in use, curved upwards of the curved portion so that the contact surfaces are provided by the curved portion and the ends are kept from contacting the growth medium surface. This minimises the risk of the potentially relative thin ends digging into the surface of the growth medium. The radius of the axially curved portion may be between 1 and 5 mm, preferably between 2 and 4 mm and most preferably about 3 mm.

It is also preferred that the lower part of each of the elongate straps is laterally curved, thus providing a laterally curved contact surface and in particular, taken in combination with the axial curvature referred to immediately above, this presents a contact surface that is curved in all contact dimension presenting an ellipsoid face to the growth medium. The laterally curved part may have a radius of between 0.25 and 1.0 mm, preferably about 0.5 mm.

The elongate straps are spaced apart to provide a gap through which liquid of the inoculum can pass. It will be understood that, in the case of the contact surface presenting an ellipsoid face, even should there be no gap between the elongate straps that liquid will still pass between adjacent straps. Nevertheless it is still preferred that the straps are spaced apart at least about 0.1 mm so that adequate sample can be left trailing the spreader device in use to allow for more effective colony separation.

The elongate straps may be no more than about 3 mm wide preferably no more than about 2.5, 2 or 1.5 mm wide.

The elongate straps are angled backwardly relative to the intended direction of movement. This also minimises the risk of the straps inadvertently breaching the surface of the growth medium. This taken together with the axial curvature minimises potential breaches where perhaps the streaking is done in a less than a smooth manner, perhaps with some stuttering where there is some instantaneous backward movement of the strap or fibre due to start of rotation that is not as smooth as might be desired. The angle may be greater than about 30° and preferably between 30 and 60° and more preferably between 40 and 50° relative to the vertical.

In one form the straps are free to flex vertically and/or horizontally independently of adjacent members, however, preferably the relative lateral movement of the lower part of each of the elongate members is constrained by a linking means. Otherwise there is a risk that the elongate members become bunched together and it is preferred that the spread of elongate members is enhanced. This may be achieved by the provision of a lower lateral member joining each of the elongate members to inhibit relative lateral movement of adjacent contact surfaces. In the case of a streaker device with elongate straps the lower lateral member may be integrally formed following the curved portion of each of the elongate strips so that in use the lower lateral member is held above the surface of the solid growth medium. This, depending on the thickness of the straps, may present a relatively rigid lower portion of the streaker device with the resilient flexibility being provided by the non-curved portions of the straps.

Following the realisation that it is possible to effect single colony separation with the formation of a single band of streaks, that is, drawing a streaker device over culture medium only once, it is anticipated that generally the streaker will only require one row of spaced contact surfaces. There may, however, be circumstances where two or more bands may be required to be formed on the same culture medium surface. This may be achieved by drawing a first band across the surface using a first streaker device, discarding the first streaker device and drawing a second band using a second streaker device. Alternatively two or more rows may be provided on the same streaker device so that the streaker device may simple be reoriented for consecutive use of the two or more rows. Thus the streaker device may simply be rotated to change orientation between a first position for contact by the first row to a second position for contact by the second row.

The streaker device is envisaged as being used with a streaker apparatus for automated streaking and accordingly preferably a connector for connection to a head of a machine extends from the common support member. The connector may be in the form of a connection socket for frictional engagement with a spigot on the head of the machine, although other forms of connection such as a bayonet fix may also be contemplated. The spigot may be part of, perhaps, a pipetting means to that the same part of the head. The same feature thus may be used for engagement with the streaker device and a pipette tip for delivering of sample to the surface of the growth medium. Whilst the streaker device is envisioned as being used in an automated streaking apparatus, forms of the streaking device may be used manually. Thus a handle may be connected via the connector to the streaking device, or alternatively it may come with a handle already attached or integrally formed with the common support member.

For an automated system, several streaking devices may be provided loaded in, for example, a cassette or magazine and fed onto or collected by a head of a streaking apparatus sequentially, prior to formation of a new band of streaks. In one configuration a plurality of streaking devices may be formed side by side and perhaps joined by a frangible link so that each streaking device can be separated from the remainder by the automated streaking apparatus. Preferably however the streaking devices will be held in a cassette in a nonconnected stack.

The streaking device may be a single use disposable product that can be thrown away or, alternatively, the materials from which it is made could be suitable for sterilisation by, for example, autoclaving or radiation sterilisation following use and cleaning.

The straps of the streaker device are so formed that they are resiliently flexible. The degree of flexibility is preferably such that the contact surfaces can flex at least 0.25 cm vertically without breaking the surface of a 1% agar growth medium. This will provide sufficient flexibility to accommodate surface variations of culture medium provided by a commercial provider. It may be however that the quality control is considerably better and less flexibility will be sufficient. Alternatively the quality control of the plates used may be poorer and the surfaces of these may slope or may be provided as varying levels as between plates, and thus a greater flexibility may be desired. Thus is may be preferred that the plastics strap can flex at least 0.5, 1 or 1.5 cm without breaking the surface of a 1% agar growth medium.

The rows of spaced contact surfaces are designed to provide for several streaks so that a band of sufficient width can be formed in order that colony separation can readily be effected whereby several isolated colonies are provided on streaking so that they can be picked for further use. For use on a standard petri plate the rows may be between about 1.5 to 4 cm long to provide for correspondingly wide bands of streaks. The rows are preferably between about 2.5 to 3.5 cm long.

The streaking device may be made wholly of plastics and perhaps moulded in one piece.

In an alternate form of the first aspect the present invention provides for a streaking device with a plurality of resiliently flexible members spaced apart in a row, free ends of the members aligned for contact with a surface of a solid growth medium. This then allows for the formation of a band of streaks with a single pass of the row of flexible members.

The streaking device in this alternate form may have two or more rows of flexible members each distinctly spaced apart radially to allow for use of the same brush to streak a first and a second band without requiring a sterilisation step between the bands. The numbers of rows of flexible members could vary depending on the number of bands required. Typically three bands are required in the streaking process, however this might be varied to be from 2 to 5. Alternatively, more rows might be provided on each streaking device so that a single device might be used for more than one sample, each on a separate petri plate.

The flexible members may be fibres such as, but not limited to, a suitable plastics material. The free ends may either be rounded or flat, preferably rounded so that the risk of damaging the surface of the solid medium is minimised. The flexibility of the fibres is preferably such that on contact with the surface of the media these will bend rather than damage the surface. It might be desired to have the fibres bent to specifically form a curve, perhaps similar to the shape that is exhibited by currently used microbiological loops. Alternatively the flexible members may take the form of flat straps whereby the free ends present either a curved or flat edge for contact with the culture medium surface. In the case of straps it is preferable that there is a gap between adjacent ones of them whereby liquid may pass between them such that the streaking brush does not carry all of the liquid of an inoculum with it.

Where the streaking device has two or more rows of flexible members, these are regularly spaced apart radially with respect to the row support member. Thus with two rows these may be positioned at 180° relative to one another, with three rows they may be positioned at 120° relative to one another and with four rows they may be positioned at 90° to one another. Whilst the above is preferable the principle concern is that there is adequate spacing between the rows so that cross contamination is avoided.

It is also preferable that the thickness of the rows is within certain parameters. Where each of the flexible members is a fibre and these are bunched together it is desired that the row is not too thick. It is preferable that the row is not thicker than about 4 mm or 3 mm and more preferably less than about 2 mm and most preferably less than about 1.5 mm.

In a second aspect the invention provides an automated streaking apparatus for streaking for single colonies of a microorganism on the surface of a culture plate using a streaking device having a row of spaced apart contact surfaces for contact with the surface of the solid growth medium being resiliently flexibly supported by a common support member, said automated streaking apparatus comprising the following elements.

i) a head including
    an inoculating means for engaging and ejecting a disposable inoculating device, and
    a streaker attachment means, for engagement with the streaker device, and for ejection of the streaker device,
  ii) a head drive means for positioning the head at a desired position,
  iii) a culture plate station for supporting a culture plate during streaking of the fluid by the streaker device,
  iv) a disposable inoculating device station to hold one or more disposable inoculating devices ready for engagement with the inoculating means,
  v) a sample container station, to hold one or more sample containers ready for insertion of a disposable inoculating device and withdrawal of the some sample,
  vi) a streaker device storage station to hold one or more streaker devices for engagement with the streaker attachment means,
  vii) a disposal station, including a disposal receptacle with an opening for receiving used disposable inoculating device and streaking devices ejected from the head,
  viii) a controller means for controlling said elements of the automated streaking apparatus,
    said controller means effecting:
      positioning of the head above a disposable inoculating device in the disposable inoculating device station, engagement of the disposable inoculating device by the inoculating means, positioning the head over a sample container in the sample container station, taking a sample from the sample container on the disposable inoculating device, positioning the head over a culture plate station supported by the culture plate station, inoculating the sample at a depot on the culture plate, positioning the head over the opening of the disposal receptacle, ejecting the disposable inoculating device into the disposal receptacle, positioning the head over the streaker device storage station, engaging a streaker device with the streaker attachment means, positioning the head over the culture plate station, contacting the surface of the culture plate and the sample depot with the streaker device, effecting relative rotation of the streaker device and the culture plate whilst said streaker device is in contact with the surface of the culture medium to streak the sample thereon, withdrawing the streaker device, positioning the head over the opening of the disposal receptacle and ejecting the streaker device into the disposal receptacle.

Preferably the disposable inoculating device is a pipette type and the inoculating means is a pipetting means for engaging the pipette tip, drawing fluid sample into the pipette tip and discharging the fluid from the pipette tip and ejection of the pipette tip. The sample depot is thus formed by appropriate deposition of the fluid sample on the surface of the culture plate surface.

Conveniently the head drive means and the head are positioned above the culture plate station, pipette station, sample container station, streaker device storage station and the disposal station, the head drive means comprising a sliding gantry supported for movement on either side by a respective rail means, the gantry being driven by a motor along the rail means to effect motion of the head in a first dimension, the head being driven by a second motor means along the gantry to effect motion of a head in a second dimension horizontally transverse to the first dimension. This may conveniently be provided over a rectangular layout of the apparatus, however alternatively the layout could be circular or semi-circular whereby the gantry is rotatable about a central vertical shaft, the culture plate station, pipette station, sample container station, streaker device storage station and the disposal station, all being spaced radially of the central vertical shaft.

The head is preferably supported on the gantry by a carriage, the head supported for being raised and lowered relative to the carriage.

The pipetting means may comprise a reversible pump in fluid communication with a downwardly facing pipette tip engaging tube. The pipette engaging tube is dimensioned for frictional engagement with a pipette tip, the pipetting means additionally having a pipette tip ejection means to urge the pipette tip from the engaging tube. The tip ejection means may take the form of a ejection member that bears against an uppermost surface of the pipette tip to apply a pressure thereon to urge the tip off of the tip engaging tube.

The connector of the streaker device preferably includes a connector socket with internal dimensions the same as the pipette tip so that the pipette tip engagement tube is also capable of engaging with the socket of the connector of the streaker device to frictionally engage therewith, and the pipette ejection means capable urging the streaker device from engagement with the pipette tip engagement means.

Where it is to be used with a streaker device with more than one row of contact surfaces the head also includes streaker device reorientation means to rotate the streaker device reorienting from a first position where a first of the rows contacts the surface of the medium, to a second position where a second of the rows of contact surfaces contact the surface of the medium.

Preferably the culture plate station includes a rotatable plate table to rotate the culture plate once the streaker device contacts the surface of the medium to thereby effect the streaking. Alternatively the culture plate may be supported by rollers which can be driven to rotate the plate. To provide an apparatus that is able to separate colonies with a single band of streaks the rotatable table is preferably controlled by the controller means to reach a speed of at least about 25 r.p.m. and more preferably of a least about 30 or 40 r.p.m.

For convenience the apparatus also has a culture plate removal means including a conveyor means for delivering the streaked agar plate to a collection receptacle. This then takes the plate off of the culture plate station and may include a means to first push the plate from the plate station this may take the form of a ram, the conveyor means may be a driven conveyor system, either in the form of rollers or a conveyor belt.

The apparatus may also provide a culture plate lid removal means to remove and replace a lid of the culture plate to be streaked. This is preferably operable at removing and replacing the lid at the culture plate station.

A fresh culture plate storage means for storage of fresh culture plates is preferably also provided whereby perhaps a cassette of preprepared culture plates are stored ready for use, they may then be taken by a fresh culture plate delivery means to the culture plate station. Two or more fresh culture plate storage means may be provided, in particular this may be required where two or more different forms of media may be required to grow the range of microorganisms concerned.

The apparatus may comprise a culture plate labelling means for labelling the culture plate with an indicium to identify the sample that has been streaked. Thus a bar code or other printed indicium can be applied to the plate concerned after or before the plate has been streaked, and may be applied on the streaking station or when the plate is being delivered or taken therefrom.

It is usual for pipette tips to be carried on a rack and thus the pipette tip station preferably includes a platform for holding a rack of pipette tips. Conveniently the apparatus also comprises a pipette tip storage means and delivery means for delivery pipette tips to the pipette tip station. Similarly it is preferred that the apparatus comprises conveyor means for removing empty pipette tip racks. Whilst it is anticipated that the pipette tips will be discarded, used pipette tips may be replaced into pipette tip rack instead for cleaning, sterilisation repackaging and reuse.

The sample container station preferably includes a means for locating a containers holding a liquid sample and closure removal means for removal of a closure of the samples may also be provided. The apparatus may also comprise container delivery means for delivery of the container holding the liquid sample to the container locating means, this may include a conveyor means such as conveyor rollers or a conveyor belt. Similarly the apparatus may further comprise container removal means for conveying a container the sample of which has been streaked to a storage depot from the sample container station.

The apparatus may also comprise streaker device storage means for storage of a plurality of streaker devices. This may take the form of a storage cassette.

Two or more culture plate stations and attendant means for delivery and removing plates therefrom may be provided, perhaps useful where two or more different types of media are to be used. One controller means may be shared between two or more automated streaker apparatuses, the controller may have a plurality of connections port means whereby streaker apparatuses can progressively be connected so that the capacity can be expanded in a modular fashion.

In an alternate second aspect the invention provides an automated streaking apparatus for effecting 2 or more bands of streaks using a streaking device with two or more rows of contact surfaces of the type referred to in any or of the embodiments referred to herein, the streaking apparatus includes a head the movement of which is controlled mechanically or by a control means such as a computer which provides instructions for the following steps; the step of lowering the streaking device so that a first row of flexible members contacts the culture medium surface, the step of effecting passage of the first row of flexible members over the surface of the culture medium to provide a first band of streaks, lifting the streaking device out of contact with the culture medium surface, reorienting either the streaking device or the container of medium; the step of rotating the streaking device so that a second row of flexible members contacts the surface of the culture medium adjacent an end of the first band of the streaks, the step of effecting passage of the second row of members over the surface of the culture medium to provide a second band of streaks, said second band of streaks initially traversing the first band and then passing onto uninoculated culture medium, followed by the step of lifting the streaking device out of contact with the culture medium.

A third or fourth or even more bands of streaks may be accommodated by the control means.

The apparatus may have an inoculating means for inoculating a sample onto the plate for subsequent contact by the first row of flexible members. Alternatively inoculation may be performed manually. The inoculum may take the form of a liquid sample whereby the inoculating means may be in the form of a pipetting means. Alternatively the sample may not be suspended, thus for example it may be picked from a colony taken from a solid growth medium, and the inoculating means may effect a streak radially of the plate. It will be understood that other forms of the invention may also contemplate the use of this inoculating means in place of a pipetting means.

The apparatus is preferably suitable for standard culture containing containers such as a round petri dish. The band may conveniently be drawn in a straight line, with the second band drawn across the first band and at an angle thereto of perhaps 45°, and any third band similarly positioned, thereby following conventional manual practice. Alternatively the bands might be drawn in an arc following the curvature of the petri dish, and the traverse of the second band is generally in line with the curvature of the first band so that sufficient inoculum is be carried along from the first band especially where the flexible members of the brush are provided at a high density.

It will be understood that the passage of the head over the medium may be achieved either by movement of the head or the container in which the medium is formed. It will be understood that this may be applicable to petri dish but equally applicable for use on solid media presented in other non-standard dishes.

The apparatus may also include sample handling means, including opening means to open sample containers, means to remove an aliquot of the sample therefrom, an inoculating means to inoculate the plate, and means to transfer the aliquot to the inoculating means.

In a further form the automated spreading apparatus includes a head for connection with a streaking device of any one of the forms set out above, the movement of which is controlled mechanically or by a computer which provides instructions for the following steps; the step of retrieving a sterile streaking device, for example, from a magazine; the step of rotating the streaking device so that the first row of elongate members extends downwardly towards the culture medium; the step of lowering the streaking device so that the first row of elongate members contacts the culture medium surface; the step of providing relative motion between the first row of elongate members and the culture medium's surface to generate the first band of streaks; the step of lifting the streaking device out of contact with the culture medium surface; the step of reorienting the streaking device and the culture medium so that they are positioned to commence the second band; the step of axially rotating the streaking device so that a second row of elongate members is perpendicular to the culture medium surface; the step of lowering the second row of elongate members so that they contact the culture medium's surface adjacent to the end of the first band of the streaks; the step of providing relative motion between the second row of elongate members and the culture medium to generate a second band of streaks, where said second row of flexible members initially traverses a part of the first band of streaks and then traverses uncontacted growth medium; the step of lifting the streaking device out of contact with the growth medium; the step of disposing of the used streaking device.

It is to be understood that the invention encompasses a method of streaking a plate using the steps set out above, or a combination of one or more sequences of such steps.

Thus in a third aspect the invention provides a method of streaking for single colonies of a microorganism on the surface of a culture plate using streaking device having a row of spaced apart contact surfaces for contact with the surface of the solid growth medium being resiliently flexibly supported by a common support member, the method including the steps of i) placing a depot of microbial containing sample in a depot on the plate ii) contacting the plate surface at the depot with the row of contact surfaces of the streaker device, and iii) drawing a band of streaks across the surface.

It is to be understood that the method encompasses the drawing of only one band of streaks on the surface of the growth medium, and that is a preferred form, the invention also encompasses the formation of a subsequent band or bands thus a second or perhaps third, fourth or more bands of streaks is formed by the step of contacting the surface of the plate with a second or further row of contact surfaces, the method including contacting the first or subsequent band, and the step of drawing a second or yet further band of streaks across the surface of the growth medium.

Drawing the bands may be achieved by drawing the streaker device in a straight path or wavy path, however preferably the band of streaks are drawn by a relative rotation of the plate and the streaking device and most preferably the rotation is of the plate.

It is found that a rotating the plate above certain speed provides for superior separation of colonies. The trials to date have been based on rotation from a stationary start thus the maximum speed of rotation has not been maintained throughout a full rotation. Furthermore the rotation was not taken through a full 360° probably more like 280-300°. It is estimated that full speed may have been attained for approximately only the last 50% of the rotation particularly at the highest speeds tested, and given the degree of separation achieved it is probably that the speed are only required for perhaps 25, 30, 35, or 40% of a traverse of 320° on a standard petri plate. The speeds tested show particularly good separation for a test sample seeded with a sample of $10^8$ organism at final speed of 40 r.p.m. or more, however the next closest speed tested was about 10 r.p.m. For more typical biological samples the density of micro-organisms is probably less, being in the order of $10^2$ to $10^5$ organism per mL. It is anticipated that final speeds of about 10 rpm preferably 15 rpm or more will result in goods separation with a single band. That the method may contemplate speeds of greater than about 10, 15, 20, 25, 30, 35, 40 r.p.m. for at least for a final 25% of the rotation, being perhaps 70° or 80° of rotation.

It is envisioned that the method will principally be used in isolating single colonies of one sample per culture plate, however two or more samples may be streaked onto portions of a culture plate. Thus two samples may be each streaked over separate halves of a plate, or three samples may be streaked over separate thirds of a plate.

BRIEF DESCRIPTION OF THE DRAWINGS

For a better understanding the invention will now be described by reference to an illustrated embodiment, wherein.

DETAILED DESCRIPTION OF THE ILLUSTRATED EMBODIMENTS OF THE INVENTION

The invention provides in a first aspect a streaker device (1) for streaking a microbial inoculum (20) for single colonies on the surface of a solid growth medium (16). The streaking device has a row of spaced apart contact surfaces (21) for contact with the surface of the solid growth medium. The contact surfaces are resiliently flexibly supported by a common support member.

Figure 1:
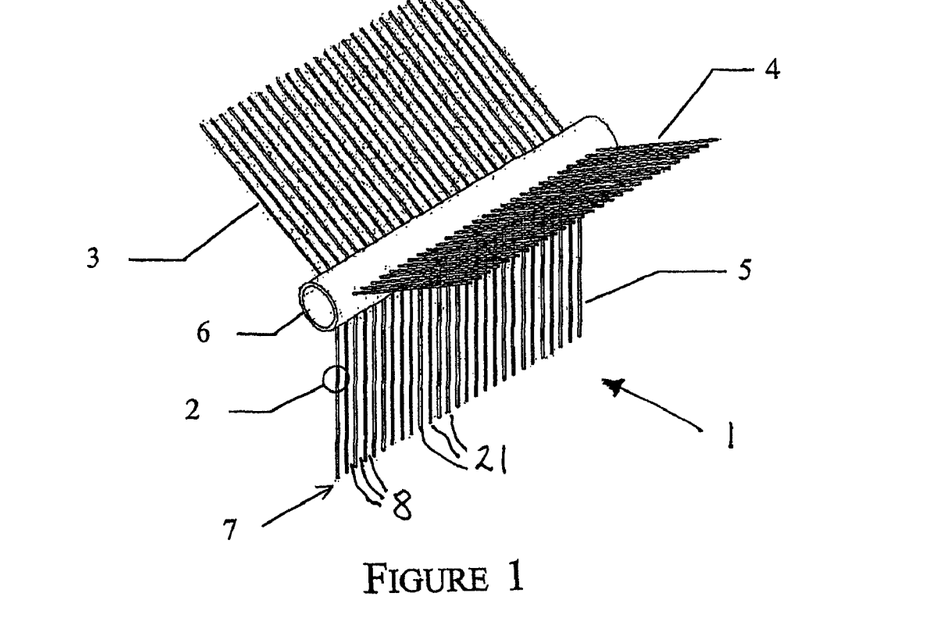
FIG. 1 is a somewhat schematic perspective view of a first embodiment of a streaking device with three rows of flexible members.
Figure 2:
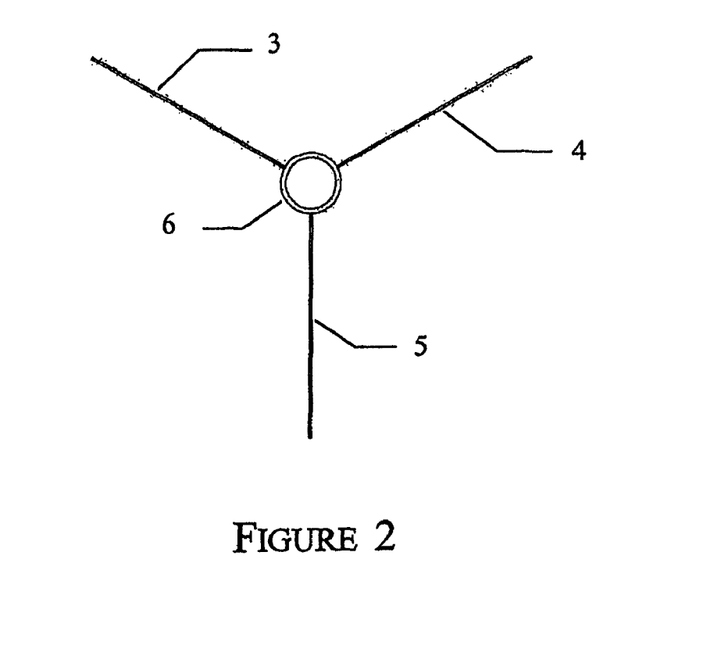
FIG. 2 is a schematic end view of the first embodiment of the streaking device of FIG. 1.
Figure 3:
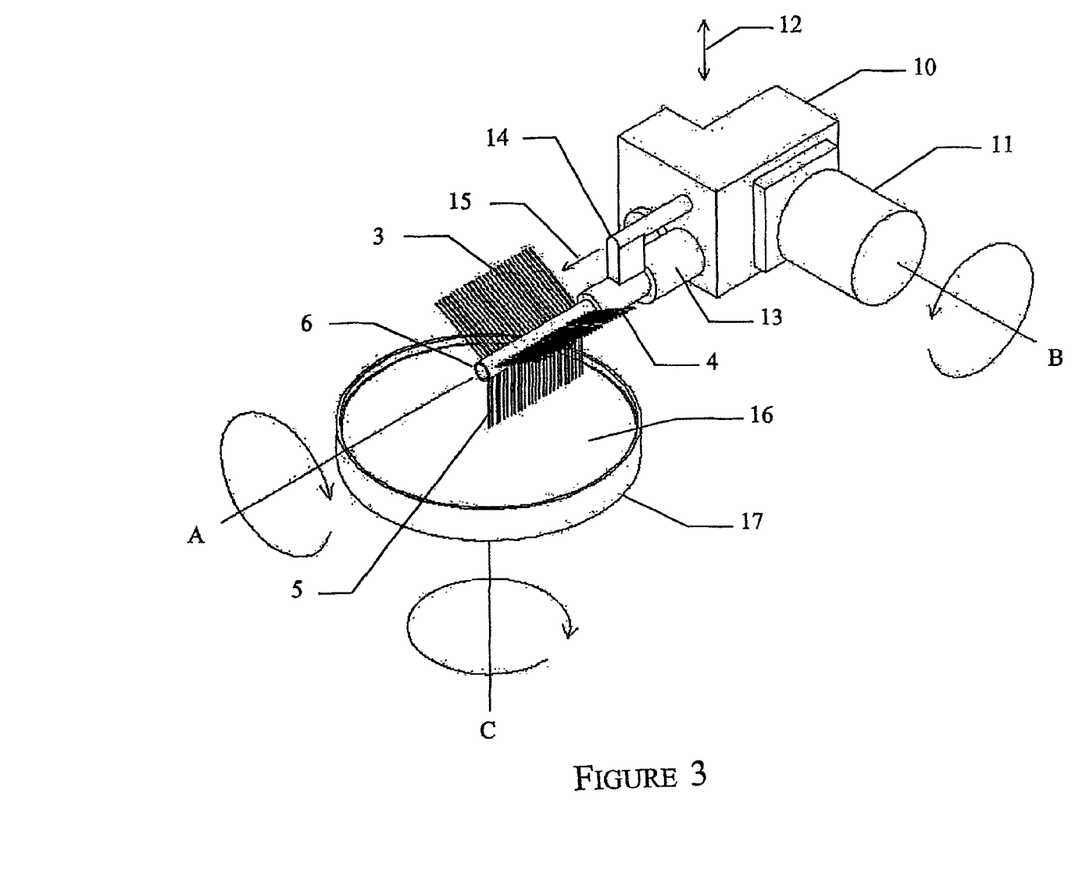
FIG. 3 is a schematic perspective view of one embodiment of a head of an apparatus with the brush connected thereto relative to a petri plate.
Figures 4, 5, 6, 7:
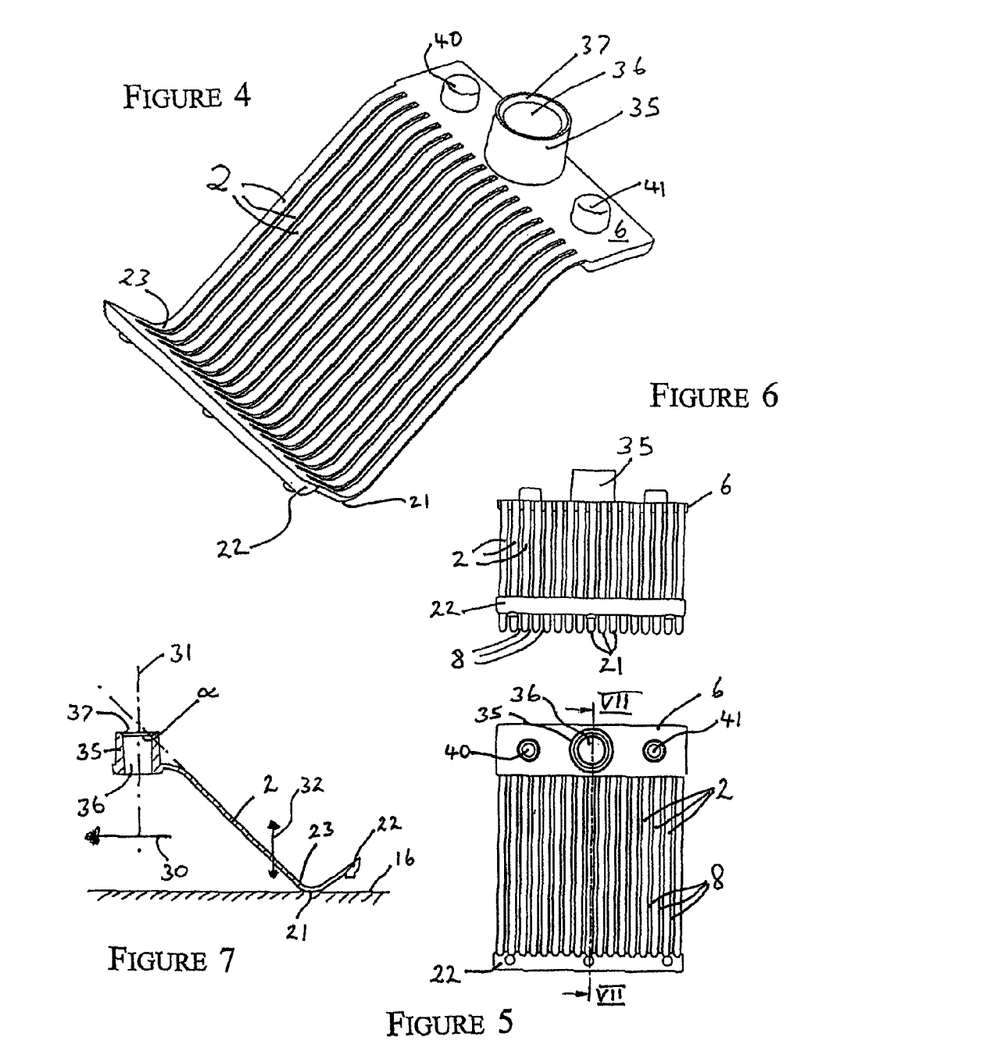
FIG. 4 is a perspective view of a second embodiment of a streaking device.
FIG. 5 is a top plan view of the second embodiment of streaking device.
FIG. 6 is a rear plan view of the second embodiment of streaking device
FIG. 7 is a cross sectional view through VII-VII of the second embodiment of streaking device.

Turning specifically to the first illustrated embodiment shown in FIGS. 1, 2 and 3, the streaking device (1) takes the form of a streaking brush which comprising elongate resiliently flexible members (2) arranged in three rows (3, 4, 5) extending radially from a the common support member (6).

The elongate members are formed from a sterilisable plastics material and have sufficient flexibility to pass over the surface of a standard agar based solid culture medium without damaging the surface thereof. The flexibility accommodates unevennesses of the surface of the medium. It can be seen that free ends (7) of the elongate members are aligned for common contact with a planar surface of medium held within a container. The flexible members of each row have gaps (8) therebetween so that at least some of the liquid of any inoculum can pass through. Each row is represented as single strands of flexible members aligned. Other forms of the invention might encompass a row with a depth of two or more, perhaps thinner strands.

The common support member (6) is positioned with the three rows extend radially therefrom. One end of the brush includes a connector (not shown) for connection either to a handle for manual operation or to a head of an automated streaking apparatus. It can be seen that the three rows of flexible members are regularly spaced apart extending at 120° from adjacent rows.

A second embodiment of the streaker device is more particularly shown in FIGS. 4, 5, 6, 7 and 10, is the preferred embodiment. This embodiment of streaker device is moulded from plastics in one piece. The elongate flexible members (2) take the form of straps extending downwardly from the common support member to form a single row. All of the straps are joined at a lowermost end by a lower lateral member (22), so that the relative lateral movement of the each of the elongate members (2) is inhibited, and in this embodiment they are firmly held in position. It can be seen that the lower lateral member is also somewhat thicker in cross section than the elongate straps (2) and it thus also inhibits relative vertical movement of the elongate straps.

It can be seen that the spaced contact surfaces (21) are not provided by ends of the elongate straps (2). Instead all of the elongate straps have an axial curved portion ((23) formed therein, the contact surface being provided at a lowermost part of the curved portion when held in a position for use, as perhaps best seen in FIG. 7. It can be seen that the ends and lower lateral member (22) are held above a surface of the growth medium (16) whereas the nadir of the axially curved portion (23) contacts the surface and thus provides the contact surface.

The curved portion provides a relatively wide curve to minimise the risk of breaking through the surface of the solid culture medium. In this second illustrated embodiment of the streaker device the contact surface has an axial radius of 3.2 mm. Each of the straps has a width of 1 mm and to additionally minimise the prospect of breaching the surface of the growth medium the elongate strap each also, at least at the curved region, are additionally transversely curved, in this embodiment they are provided with a curvature with a radius of 0.5 mm. This can perhaps best be seen in FIG. 6. The contact surface thus presents a compound curved surface to the surface of the solid growth medium that might be described as elliptoidal. Accordingly no abrupt changes in shape are presented to the medium with attendant potential for the media surface to be breached.

It can also be seen that each of the elongate straps (2) are spaced apart from adjacent straps to form gaps (8) therebetween, the gaps are approximately 0.1 mm at the upper surface thereof. It will be understood that the gaps are wider at the lower surface of the elongate straps because the curvature provides a radial divergence of the gap by reason of the lateral curvature of the elongate straps. This provides a considerable gap, approximately triangular in cross section, through which a liquid inoculum can pass.

The elongate straps extend backwardly relative to the direction of travel (30) from the vertical (31), at an angle α of approximately 45°. The backward angling reduces the prospect of damage to the growth medium surface, and also facilitates the capacity of the elongate arms to flex (32) vertically, to accommodate variations in the surface, or variations in fitting of the spreader device to an automated spreading apparatus, where perhaps there are variations in the vertical height of engagement. The streaker device is made of High Density Polyethylene (HDPE) Asrene SI5230 and has a vertical flex of about 1 cm before there is a risk of breaking though the surface of a 1% agar plate that have been suitably dried.

The elongate straps extend downwardly from the common support member (6). As can be seen the common support member is about twice the thickness as the elongate straps at about 4 mm compared to about 2 mm. This provides a relatively rigid support for all of the elongate straps (2). Central to the common support member is an upwardly extending connector (35) with a central bore (36). An uppermost portion of the bore has a taper (37) to facilitate location of an attachment means in the form of a spigot on the head of a streaking apparatus. The bore is also slightly tapered from lowermost to topmost end, being at 3.5°, which facilitates the frictional fit by which the connector engages the attachment means spigot.

The common support member also provides rotation inhibition means in the form to two spaced apart protrusions (40, 41) with corresponding bores on an underside to assist with the positive positioning of the streaker devices to ensure correct orientation before engagement with the head.

Figure 8:
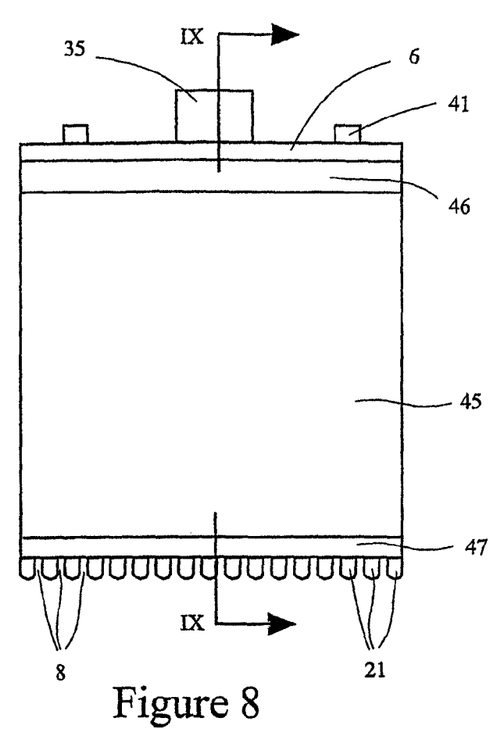
FIG. 8 is a top plan view of a third embodiment of a streaking device.
Figure 9:
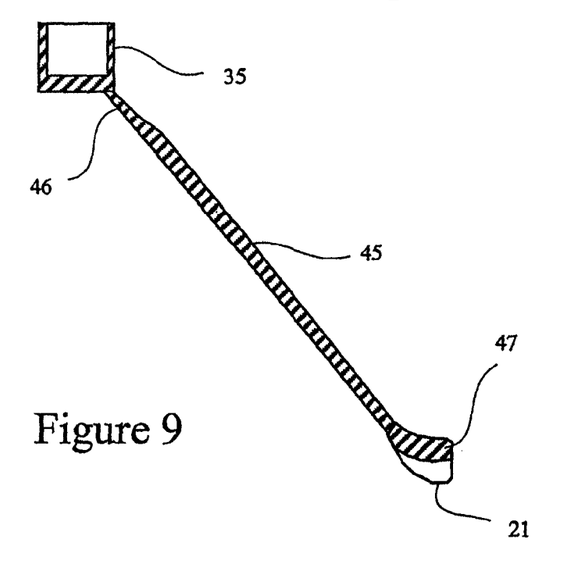
FIG. 9 is a cross sectional view through IX-IX of the third embodiment of the streaking device.

A third embodiment of streaker is illustrated in FIGS. 8 and 9. This embodiment differs from the first two embodiment in that this does not provide for elongate members. This third embodiment provides a common support member (35) very similar to that of the second embodiment. In place of elongate straps extending downwardly from the common support member a web support (45) extends downwardly. The web is principally of relatively rigid construction apart from a thinned portion (46) adjacent the common support member (35). The thinned portion is resiliently flexible and provides for vertical flex of the contact surfaces (21).

The contact surfaces (21) are formed beneath a curved surface support member (47) which is relatively rigid in construction. The contact surfaces are radiused laterally as can be seen in FIG. 8, as well as axially to enhance the capacity for vertical flex without breach of a solid growth medium surface.

Figure 10:
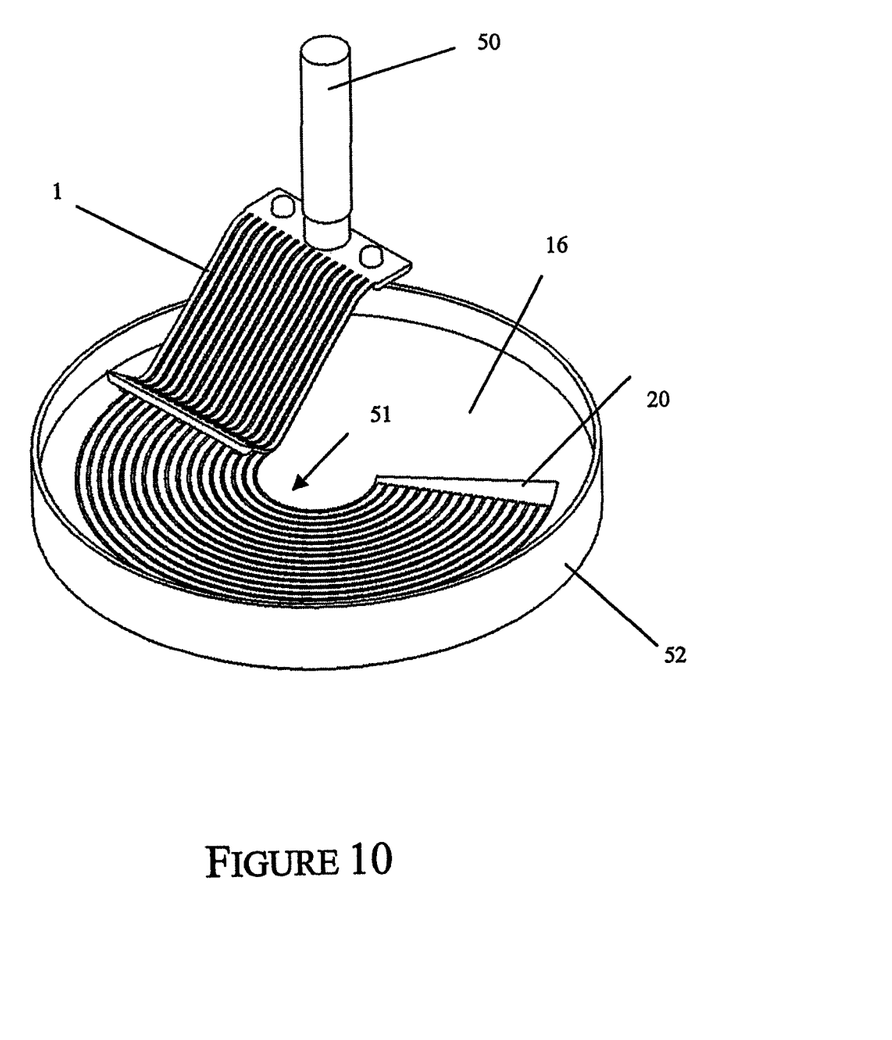
FIG. 10 shows the second embodiment of streaking device effecting a streak on a petri plate of solid culture medium.

FIG. 10 shows the manner in which the second embodiment may be used to streak the surface of solid growth medium in a petri plate (52) manually. An initial inoculum (20) is placed on the surface of the plate in a radial line. A handle (50) is attached to the connector, and the contact surfaces (21) of the streaker device are contacted onto the line of initial inoculum. The petri dish is supported on a rotor table (not shown) which is actuated to turn the petri dish in the direction indicated by the arrow to thereby draw streaks of inoculum along an arcuate band (51). The streaker device can then be lifted from the plate, a cover replaced and the plate can then be placed in an incubator to grow the colonies.

More typically it is envisioned that the streaker device will be used in the context of an automated streaking apparatus. A head (10) of an automated apparatus can be seen in FIG. 3. The head is connected rotatably (about axis B) to a support (not shown) via an incrementally adjustable connector (11) that might, for example, be driven by a stepper motor. The whole head may be raised and lowered vertically (as shown by arrow 12) by means not shown.

An attachment means (13) attaches to the common support of the brush which extends from the flexible member support.

The connector may provide a snap fit connection. A brush ejector (14) is movable axially with respect to the brush in the direction shown by arrow (15) to overcome the grip exerted by the connector and thereby remove the brush from the head. The connector is rigidly connected to the brush so that together they may be incrementally rotated about axis A for alignment of the rows of brushes for contact with the surface of the culture medium (16) held in the plate (17). A plate support (not shown) is also incrementally rotatable about axis C.

A plate is positioned with its lid off at the culture plate station. A pool of inoculum perhaps in the form of a radial line is deposited onto the growth medium in a depot 20. A streaker device is fitted onto the connector. The streaker device is oriented so that a first row of flexible members extends towards the surface of the solid culture medium. The head is lowered so that free ends of the first row of contact surfaces contacts the surface of the culture medium in, or upstream of, the depot of inoculum. The plate can be rotated so that the ends of the flexible members describe an arc on the plate carrying with it some of the inoculum. The streaker means can be lifted, the attachment means and streaker device reoriented through 120°, the position of the plate reversed by perhaps 1 cm the second row of elongate members lowered to contact the surface of the medium and the plate is rotated again initially contacting the first band of streaks for the 1 cm or so and then passed over uninoculated medium. The process is repeated a third time with the third row of elongate members. The streaker device is lifted and removed and deposited into a suitable disposal receptacle for cleaning or recycling. The lid is replaced onto the inoculated plate and transported to an incubator.

Figure 11:
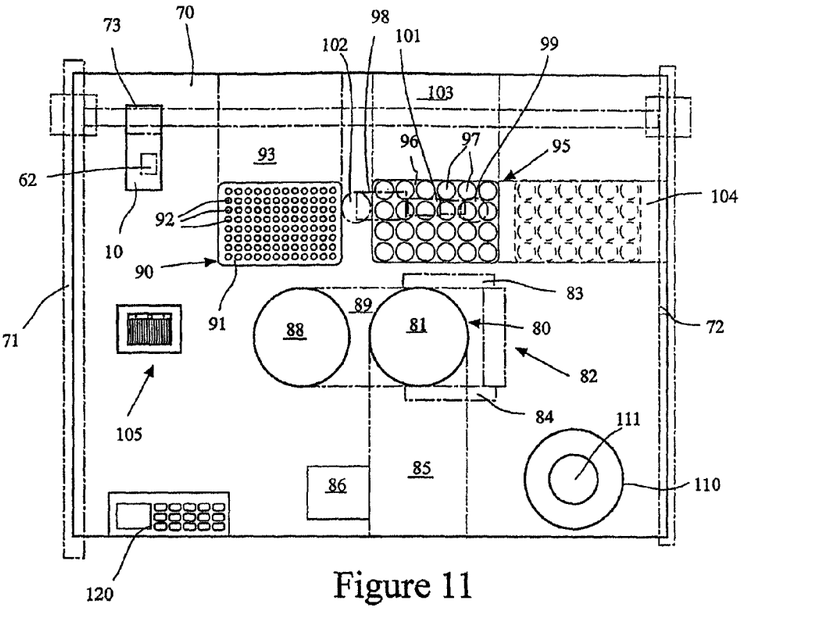
FIG. 11 is a schematic plan view from above of a streaking apparatus for effecting automated streaking of micro-organisms onto solid culture medium.
Figure 12:
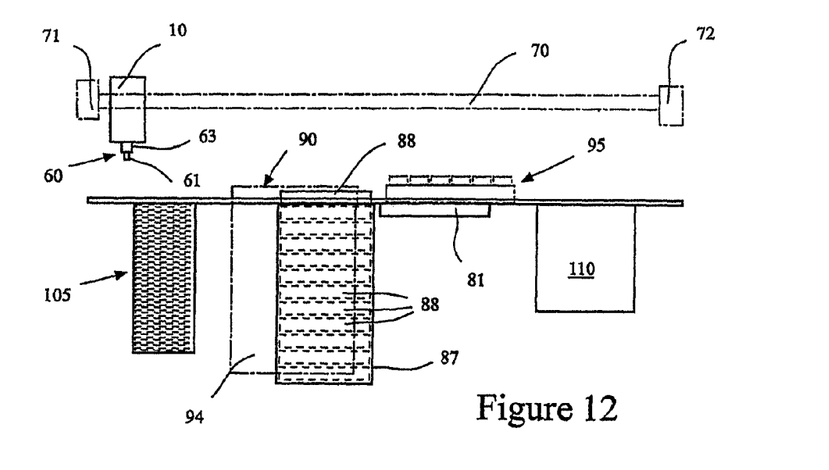
FIG. 12 is a schematic side plan view of the streaking apparatus of FIG. 10.

FIGS. 11 and 12 are schematic representations of an automated streaking apparatus using a streaking device. The streaking apparatus includes a head (10), the head including a pipetting means (60) which includes a pipette tip engaging tube (61) which operates to frictionally engage a pipette tip, the pipette tip tube is in fluid communication with a reversible pump (62) which operates to draw fluid into the pipette tip and on reversal to discharge fluid from the pipette tip. The pipetting means further comprises an ejection collar (63) to bear against an upper edge of the pipette tip to urge the tip from frictional engage with the pipette tube and thereby eject the tip. The head also includes a streaker attachment means for engagement with the streaker device. The bore (36) in the connector (35) of the second embodiment has the same internal dimensions as the pipette tip and thus the pipette tip engaging tube can also frictionally engage with the streaker device. To prevent rotation of the streaker device relative to the head, the streaker device has rotation inhibition means in the form of two spaced apart protrusions (40, 41) which register in to correspondingly shaped depressions in the head (not shown). The streaker device can be ejected by the same element of the head as the pipette tip, thus the ejection collar can bear against the upper surface of the connector to urge the spreader device from the pipette tube and to thus be ejected.

A head drive means comprises a gantry (70) along which the head can be driven from side to side across the generally rectangular working area of the streaking apparatus. The gantry is supported on either side by two rails (71, 72), one or two motors can drive the gantry along the length of the rails. Thus it will be appreciated that the head can be positioned anywhere within the generally rectangular working area. The head can also be moved vertically relative to a carriage (73) which is fixed relative to the gantry (70).

A culture plate station (80) is provided to support a culture plate during streaking. The culture plate station comprises a rotatable table (81) whereby the culture plate can be rotated relative to the streaker device when held in contact with a surface of the culture medium. A culture plate cover remover (82) is provided to remove the cover of the culture plate in readiness for the streaking operation. Two arms (83, 84) contact the cover and flip the cover in an inverted position during inoculating and streaking operations before replacing the lid when the operation is finished. A culture plate removal means comprises a culture plate removal conveyor (85), and perhaps a ram (not shown) to slide the culture plate from the culture plate station onto the culture plate removal conveyor. The streaked culture plates will be collected, in for example a basket which once the desired number of plates have been collected can be conveyed to an incubator. A culture plate labeller (86) is positioned adjacent the culture plate removal conveyor to label the culture plate with indicia indicative of the sample that was streaked thereon.

A fresh culture plate storage means may be provided by a fresh culture plate cassette (87) storing a stack of fresh culture plates (88) this may be spring loaded to deliver one fresh culture plate above the working surface of the streaking apparatus at a time. A fresh culture plate delivery means comprises a fresh plate conveyor (89) to convey the fresh culture plate to the culture plate station.

A pipette tip station (90) comprises a platform to hold a tray (91) of pipette tips (92) open upwards ready for engagement by the pipetting tube. A pipette tray removal conveyor (93) removes pipette trays from the pipette tip station once all the pipette tips in the tray have been used. A pipette tip cassette (94) stores a stack of trays of unused pipette tips, and once the tray in the pipette tip station is removed, a new tray is fed upwards to be located on the platform.

A sample container station (95) comprises a platform to hold a tray of (96) sample containers (97). A container lid remover (98) is provided to remove and replace the screw capped lid of the sample container to be sampled. A head (99) of the lid remover grips the periphery of the lid, and rotates anticlockwise and clockwise to remove and replace the lid. A telescoping arm (101) on a vertical pivotal shaft (102) positions the lid remover to the appropriate sample.

A sample removal conveyor (103) conveys trays from the sample container station (95) and a fresh sample conveyor (104) feeds samples to the container station when the sample container station has no samples tray thereon.

A streaker device supply station (105) provides a cassette of unused streaker devices an uppermost one of which is positioned for engagement by the head (10) of the streaking apparatus. A disposal station (110) comprises a disposal container (111) into which used streaker devices and/or pipette tips can be discarded.

A controller (120) is linked with all elements of the streaker apparatus to control their action. Principally this will be automatically controlled, however it may be necessary to have a manual operating mode.

Feedback means may also be provided strategically placed to interrogate the status of the individual elements. Thus feedback may be provided to ascertain when the various operating stations such as the sample tray station, pipette tray stations are occupied or not. Similarly feedback means may be desired to determine whether the plate cassette, streaker device cassette or the pipette tip cassette is empty. A pressure sensor may be provided to ascertain when the streaker device has made contact with the surface of the culture container.

A message may be provided on a change in status, which may be an alert or it may be to actuate a feed through to an empty station.

Figure 14:
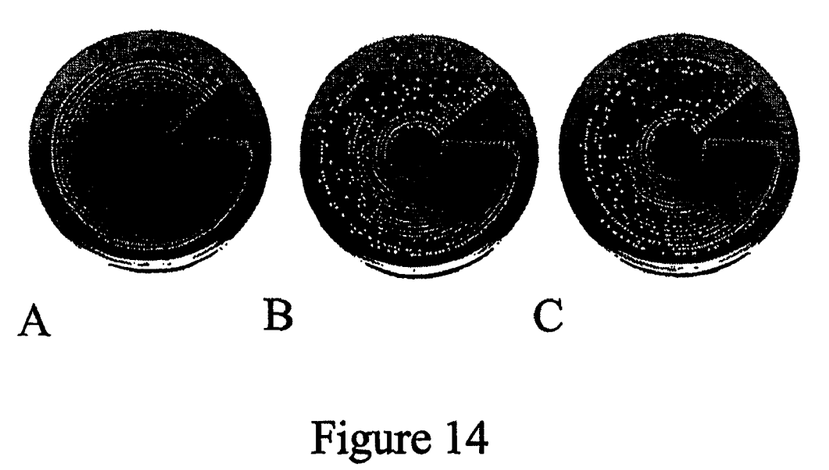
FIG. 14 shows colony separation that can be effected at differing speeds of rotation of the plate.

A trial was conducted using the streaker device of the second illustrated embodiment to ascertain whether isolated colonies could be achieved by drawing a single band around a plate. An inoculum of 15 µl of $10^9$ *Escherichia coli* cells were inoculated in a radial line as a primary inoculum. The streaker device was contacted at the primary inoculum and from a standing start accelerated to three speeds, (A) 8, (B) 40 and (C) 80 r.p.m. It is estimated that all of these speeds were achieved for about one half of the rotation that was undertaken. The extent of rotation is estimated to be approximately 320°. It can be seen that good separation was achieved at 40 r.p.m. It is anticipated that good separation will also be achieve with lower speeds perhaps as low as 20 r.p.m. An indication of the colony separation achieved can be seen in FIG. 14.

Figure 13:
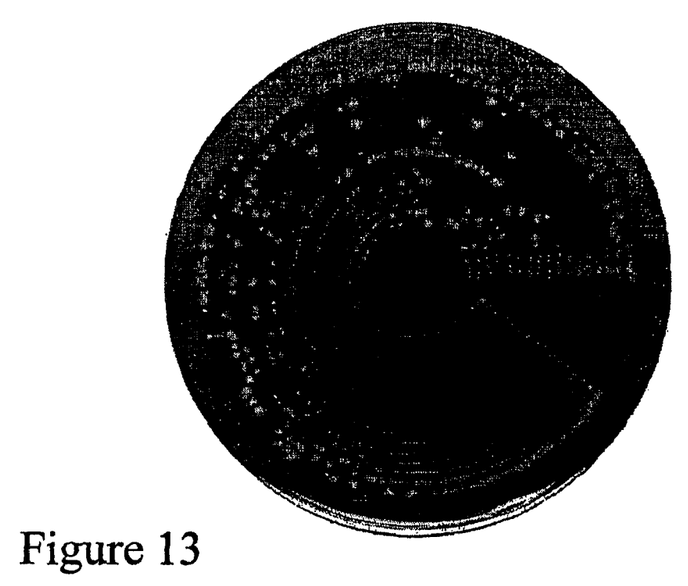
FIG. 13 shows separation of colonies that can be formed using an illustrated embodiment of the invention with two cultures at differing concentration.

FIG. 13 shows separation of a mixed culture of $10^8$ *Staphylococcus epidermidis* and $10^9$ *Escherichia coli*. It can be seen that both types of bacteria exhibited separation, the *S. epidermidis* (small colonies) were separated as was the *E. coli* (large colonies). The rotational speed used was 80 rpm.

Various features of the invention have been particularly described in connection with the exemplified embodiments of the invention, however, it must be understood that these particular arrangements merely illustrate and that the invention is not limited thereto and can include various modifications falling within the spirit and scope of the invention.

The invention claimed is:

1. A streaker device for streaking a microbial inoculum for single colonies on the surface of a solid growth medium, said streaker device having a row of spaced apart contact surfaces for contact with the surface of the solid growth medium being resiliently flexibly supported by a common support member, wherein the contact surfaces are provided one each on an elongate member, and wherein relative lateral movement of the lower part of each of the elongate members is constrained by a linking means.

2. The streaker device as in claim 1 wherein each elongate member is a fibre.

3. The streaker device as in claim 1 wherein each elongate member is a strap.

4. The streaker device as in claim 3 wherein the streaker device is made of plastics and moulded in one piece.

5. The streaker device as in claim 3 wherein the strap is flexible.

6. The streaker device as in claim 3 wherein each elongate strap has a thinning to provide a flexible hinge region.

7. The streaker device as in claim 1 wherein an axially curved portion is formed into a lower part of each of the elongate members, the contact surface being provided at the curved portion.

8. The streaker device as in claim 7 wherein the axially curved portion has a radius is between 1 and 5 mm.

9. The streaker device as in claim 3 wherein the lower part of each of the elongate straps is laterally curved.

10. The streaker device as in claim 9 wherein the lateral curved part has a radius of between 0.25 and 1.0 mm.

11. The streaker device as in claim 9 where the laterally curved part has a radius of about 0.5 mm.

12. The streaker device as in claim 3 wherein the elongate straps are spaced apart at least about 0.1 mm.

13. The streaker device as in claim 1 wherein the elongate straps are no more than about 3 mm wide.

14. The streaker device as in claim 1 wherein the elongate straps are no more than about 2 mm wide.

15. The streaker device as in claim 1 wherein the elongate straps are angled backwardly relative the intended direction of movement.

16. The streaker device as in claim 15 wherein the angle is between 30 and 60° relative to the horizontal.

17. The streaker device as in claim 15 wherein the angle is between about 40 and 50° relative to the horizontal.

18. The streaker device as in claim 1 wherein the straps are free to flex vertically independently of adjacent members.

19. The streaker device as in claim 7 wherein the linking means comprises a lower lateral member joining each of the elongate members to inhibit relative lateral movement of adjacent contact surfaces.

20. The streaker device as in claim 19 wherein the lower lateral member is integrally formed following the curved portion of each of the elongate members so that in use the lower lateral member is held above the surface of the solid growth medium.

21. The streaker device as in claim 1 wherein a connector for connection to a head of a machine extends from the common support member.

22. The streaker device as in claim 3 wherein each elongate strap can flex at least 0.25 cm without breaking the surface of a 1% agar growth medium.

23. The streaker device as in claim 1 wherein the rows are between about 1.5 to 4 cm long.

24. An automated streaking apparatus for streaking for single colonies of a microorganism on the surface of a culture plate using a streaker device as in claim 1, said automated streaking apparatus comprising the following elements:
   i) a head including
      an inoculating means for engaging and ejecting a disposable inoculating device, and
      a streaker attachment means, for engagement with the streaker device, and for ejection of the streaker device,
   ii) a head drive means for positioning the head at a desired position,
   iii) a culture plate station for supporting a culture plate during streaking of the fluid by the streaker device,
   iv) a disposable inoculating device station to hold one or more disposable inoculating devices ready for engagement with the inoculating means,
   v) a sample container station, to hold one or more sample containers ready for insertion of a disposable inoculating device and withdrawal of the some sample,
   vi) a streaker device storage station to hold one or more streaker devices for engagement with the streaker attachment means,
   vii) a disposal station, including a disposal receptacle with an opening for receiving used disposable inoculating device and streaker devices ejected from the head,
   viii) a controller means for controlling said elements of the automated streaking apparatus,
   said controller means effecting:—
   positioning of the head above a disposable inoculating device in the disposable inoculating device station, engagement of the disposable inoculating device by the inoculating means, positioning the head over a sample container in the sample container station, taking a sample from the sample container on the disposable inoculating device, positioning the head over a culture plate supported by the culture plate station, inoculating the sample at a depot on the culture plate, positioning the head over the opening of the disposal receptacle, ejecting the disposable inoculating device into the disposal receptacle, positioning the head over the streaker device storage station, engaging a streaker device with the streaker attachment means, positioning the head over the culture plate station, contacting the surface of the culture plate and the sample depot with the streaker device, effecting relative rotation of the streaker device and the culture plate whilst said streaker device is in contact with the surface of the culture medium to streak the sample thereon, withdrawing the streaker device, positioning the head over the opening of the disposal receptacle and ejecting the streaker device into the disposal receptacle.

25. The automated streaking apparatus of claim 24 wherein the disposable inoculating device is a pipette tip and the inoculating means is a pipetting means for engaging the pipette tip, drawing fluid sample into the pipette tip and discharging the fluid from the pipette tip and ejection of the pipette tip.

26. The automated streaking apparatus of claim 25 wherein the head drive means and head are positioned above the culture plate station, pipette station, sample container station, streaker device storage station and the disposal station, the head drive means comprising a sliding gantry supported for movement on either side by a respective rail means, the gantry being driven by a motor along the rail means to effect motion of the head in a first dimension, the head being driven by a second motor means along the gantry to effect motion of a head in a second dimension horizontally transverse to the first dimension.

27. The automated streaking apparatus of claim 26 wherein the head is supported on the gantry by a carriage, the head supported for being raised and lowered relative to the carriage.

28. The automated streaking apparatus of claim 25 wherein the pipetting means comprises a reversible pump in fluid communication with a downwardly facing pipette tip engaging tube said engaging tube dimensioned for frictionally engagement with a pipette tip, the pipetting means additionally having a pipette tip ejection means to urge the pipette tip from the engaging tube.

29. The automated streaking apparatus of claim 28 wherein a connector of the streaker device includes a connector socket with internal dimensions the same as the pipette tip so that the pipette tip engagement tube is also capable of engaging with the connector socket of the streaker device to frictionally engage therewith, and the pipette ejection means capable of urging the streaker device from engagement with the pipette tip engagement means.

30. The automated streaking apparatus of claim 25 wherein the head includes streaker device reorientation means to rotate the streaker device, the streaker devices having two or more rows contact surface, the rotating from a first position where a first of the rows contact the surface of the medium, to a second position where a second of the rows of contact surfaces contact the surface of the medium.

31. A method of streaking for single colonies of a microorganism on the surface of a culture plate using streaker device as in claim 1, the method including the steps of:
  placing an inoculum of microbial containing sample in a depot on the plate,
  ii) contacting the plate surface at the depot with the row of contact surfaces of the streaker device, and
  iii) drawing a band of streaks across the surface.

32. The method of streaking for single colonies according to claim 31 wherein drawing the band of streaks is achieved by a relative rotation of the plate and the streaker device.

33. The method of streaking for single colonies according to claim 32 wherein the rotation is of the plate.

34. The method of streaking for single colonies according to claim 32 wherein a speed of the rotation is at least about 10 r.p.m.

35. The method of streaking for single colonies according to claim 32 wherein a speed of the rotation is at least about 35 r.p.m, for at least for a final 25% of the rotation.

36. The method of streaking for single colonies according to claim 34 wherein the speed of the rotation is maintained for an arc of at least about 80°.

* * * * *